(12) United States Patent
Broyles et al.

(10) Patent No.: US 6,419,414 B1
(45) Date of Patent: Jul. 16, 2002

(54) CONTAINER FOR MULTIPLE-COMPONENT COMPOSITIONS

(75) Inventors: Bruce R. Broyles, Oakdale; Robert W. Petrich, Woodbury; Robert Lee, Lake Elmo; Darin J. Meyertholen, Woodbury, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/838,875

(22) Filed: Apr. 20, 2001

(51) Int. Cl.[7] ................................................ B43K 5/14
(52) U.S. Cl. ........................ 401/132; 401/134; 206/219
(58) Field of Search ................................ 401/132–135, 401/123, 127–130; 206/219, 222

(56) References Cited

U.S. PATENT DOCUMENTS

| | | |
|---|---|---|
| 2,612,163 A | 9/1952 | Norman |
| 2,624,011 A | 12/1952 | Stern |
| 2,862,616 A | 12/1958 | Capozzi et al. |
| 3,340,873 A | 9/1967 | Solowey |
| 3,359,361 A | 12/1967 | Oakman |
| 3,554,705 A | 1/1971 | Johnston et al. |
| 3,613,697 A | 10/1971 | Andrews |
| 4,152,269 A | 5/1979 | Babson |
| 4,537,303 A | 8/1985 | Muhlbauer |
| 4,828,419 A | 5/1989 | Porter et al. |
| 4,845,923 A * | 7/1989 | Donovan ..................... 206/365 |
| 4,912,048 A * | 3/1990 | Smith et al. ................. 206/219 |
| 4,952,204 A | 8/1990 | Korteweg |
| 5,322,165 A * | 6/1994 | Melker et al. ............... 206/365 |
| 5,514,120 A | 5/1996 | Johnston et al. |
| 5,660,273 A | 8/1997 | Discko, Jr. |
| 5,735,437 A | 4/1998 | Broyles et al. |
| 5,743,736 A | 4/1998 | Folko et al. |
| 5,860,806 A | 1/1999 | Pranitis, Jr. et al. |
| 5,874,045 A | 2/1999 | Chisum |
| 5,989,229 A | 11/1999 | Chiappetta |
| 6,095,813 A | 8/2000 | Broyles |
| 6,105,761 A | 8/2000 | Peuker et al. |

FOREIGN PATENT DOCUMENTS

WO   WO 99/65704   12/1999

OTHER PUBLICATIONS

Microbrush, "Dispenser Series Disposable Applicator", 1 page.
Microbrush & Ultrabrush, "Dispenser Series Instructions for Assembly", 1 page.
Microbrush, ProTouch, Disposable Touch–Up Microbrush.
Pending U.S. Ser. No. 09/838,883, filed Apr. 20, 2001.

* cited by examiner

Primary Examiner—Gregory L. Huson
Assistant Examiner—Tuan Nguyen
(74) Attorney, Agent, or Firm—James D. Christoff (57) ABSTRACT

A container includes an inner chamber and one or more compartments that hold components of a composition apart from each other until needed for use. The container includes two or more sheets that are ruptured for mixing the components together when desired. In certain embodiments, the container includes an inner surface with a plurality of protrusions to facilitate mixing and dispensing of the mixed composition. In other embodiments, the container includes an articulated holder that enables the user to adjust the configuration of the container to any one of a number of orientations.

19 Claims, 4 Drawing Sheets

Fig. 11

CONTAINER FOR MULTIPLE-COMPONENT COMPOSITIONS

BACKGROUND OF THE INVENTION

1. Field of the Invention

This invention relates to a storage and dispensing container for compositions that are made of two or more components. This invention also relates to a dispensing assembly that includes a container and an applicator for dispensing a composition from the container.

2. Description of the Related Art

A variety of compositions are sold to consumers or other end users in packages or containers that keep certain components of the composition isolated from each other until the composition is needed for use. For example, epoxy-based adhesives are widely available in packages that include two compartments or containers that keep components of the adhesive initially separate. The components are not mixed together until the adhesive is needed, because once the components come into contact with each other a chemical reaction is undertaken that eventually turns the mixed composition into a hardened mass.

Containers for multiple component compositions are also widely used in the field of medicine and dentistry, including orthodontia. For example, many adhesives and cements used in dentistry are made of two liquid components that are initially kept apart from each other. Examples of two-component dental compositions include RelyX ARC dental cement and F2000 primer/adhesive, both from 3M Company.

In the past, some storage and dispensing containers for multiple-component compositions were relatively large and contained a sufficient quantity of the components for multiple applications at different times. Examples of such bulk containers include cans and jars. In use, a portion of the total quantity of each component would be measured and withdrawn from each container and transferred to a mixing location, such as a mixing well or mixing pad. Such bulk containers are in widespread use in certain applications because the costs of packaging the components are relatively low.

However, the practice of supplying multiple-component compositions in two initially separate bulk containers is not entirely satisfactory. If, for example, the user does not withdraw components from the bulk containers in the proper ratio, the characteristics of the resulting composition may be significantly impaired. Additionally, the portions of the components that remain in the container may be adversely affected over a period of time by exposure to the atmosphere once the container is opened. Furthermore, the user is often compelled to dispose of the mixing well, pad or other mixing structure after a single use, or undergo an effort to clean the same in preparation for a subsequent use.

In recent years, there has been increased interest in "single use" or "single dose" containers for compositions made of two components that are initially kept apart from each other. Such containers typically avoid the need to measure out separate quantities of each component before mixing and help assure that the components, when mixed, are present in the desired ratio. Additionally, if the components are mixed together within the container, the need for a mixing well, mixing pad or other type of mixing structure is avoided.

Examples of containers that are especially suitable for isolated storage of components for multiple component compositions are described, for example, in U.S. Pat. Nos. 5,735,437 and 5,743,736.

SUMMARY OF THE INVENTION

The present invention is related to an improved storage, mixing and dispensing container for compositions that are made of two or more components. The container is especially suitable for single-use applications, such as those found in the field of dentistry. In certain aspects, the container of the invention includes a surface having protrusions for facilitating mixing of the components. Other aspects of the invention are directed toward a container with an improved applicator, a container with an improved outer configuration, an articulated container and related methods.

In more detail, the present invention is directed in one embodiment toward a storage and dispensing container that comprises a housing having wall sections defining a chamber with an opening. A first sheet extends across the chamber and is connected to the housing, and a second sheet extends across at least a portion of the first sheet and is connected to the housing. A compartment is located between the first sheet and the second sheet. A first component is received in the chamber, and a second component is received in the compartment. The first sheet and the second sheet are rupturable in order to enable the first component to mix together. At least a portion of the wall sections include a plurality of protrusions for facilitating mixing of the components.

The present invention is also directed in another embodiment toward a storage and dispensing container. In this embodiment, the container includes a housing having side wall sections presenting an internal wall surface and an external surface opposite the internal surface. The housing also has a chamber surrounded by the internal wall surface. The chamber has a central longitudinal axis and an opening. The container also includes a first sheet that extends across the chamber and is connected to the housing, and a second sheet that extends across at least a portion of the first sheet and is connected to the housing. A compartment is located between the first sheet and the second sheet. A first component is received in the chamber, and a second component is received in the compartment. The first sheet and the second sheet are rupturable in order to enable the first component and the second component to mix together. The longitudinal axis of the chamber is inclined upwardly toward the opening when the external wall surface of the housing is lying in a horizontal plane.

The present invention is also directed to a storage and dispensing assembly. The assembly comprises a container including a housing having an internal wall surface with an opening. The container also includes at least one component of a composition received in the chamber and at least one sheet extending across the chamber and connected to the housing. Each sheet is rupturable in order to access each component. The assembly also comprises an applicator having an elongated shaft and an outer tip. The applicator also includes structure spaced from the tip and extending outwardly from the shaft in order to facilitate rupturing of each sheet as the tip is moved into the chamber.

Another embodiment of the present invention is directed toward a method of dispensing a composition made from two or more components. The method includes the act of providing a container having an elongated chamber with a first component and a compartment with a second component, wherein the first component and the second component are initially separated from each other. The method also includes the act of fracturing a rupturable sheet located between the chamber and the compartment with an applicator in order to enable the first component and the second component to contact each other. The method further includes the act of moving a tip of the applicator along a longitudinal axis of the chamber in order to mix the first component and the second component. The act of moving the tip of the applicator along the longitudinal axis of the chamber includes the act of moving the first component and the second component adjacent a surface having a plurality of protrusions in order to facilitate mixing of the components.

The present invention is also directed in another embodiment toward a method of dispensing a composition from a container. In this embodiment, the method includes the act of providing a container having a chamber with an opening and a rupturable sheet extending across the chamber. The method also includes the act of providing an applicator having an elongated shaft, a tip connected to one end of the shaft and protruding structure connected to the shaft at a location remote from the tip. The method further includes the act of pressing the tip of the applicator against the sheet in order to rupture the sheet and create an aperture. The method additionally includes the act of moving the tip of the applicator through the aperture and into the chamber in order to access a composition in the chamber. The act of moving the tip into the chamber includes the act of urging the protruding structure of the applicator against the sheet in order to enlarge the aperture that was created by the tip.

These and other aspects of the invention are described in more detail in the paragraphs that follow and are illustrated in the accompanying drawings.

DETAILED DESCRIPTION OF THE PREFERRED EMBODIMENTS

Figure 1:
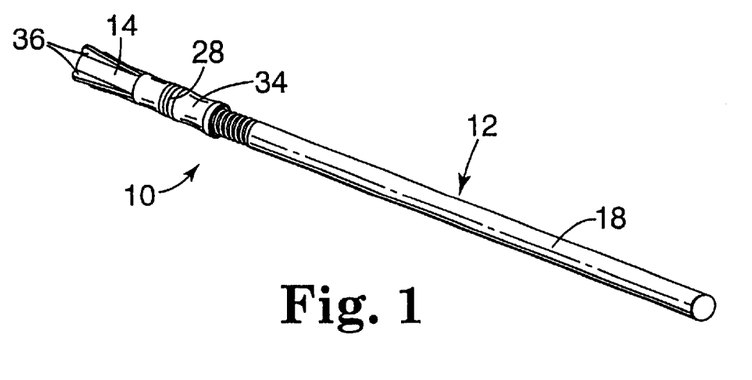
FIG. 1 is an exploded perspective view of a storage and dispensing container for multiple-component compositions according to one embodiment of the present invention.
Figure 2:
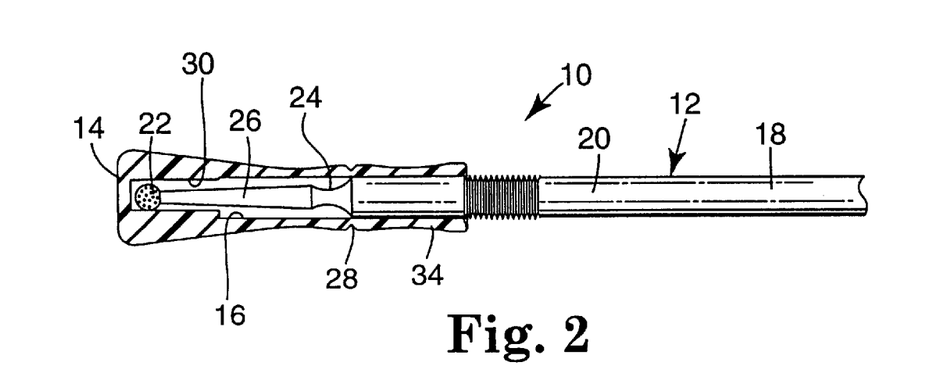
FIG. 2 is a side-cross sectional view of the container illustrated in FIG. 1 as it appears when assembled.

A storage and dispensing container according to one embodiment of the invention is illustrated in FIGS. 1 and 2 and is broadly designated by the numeral 20. The container 20 includes a housing 22 that is preferably relatively rigid. Preferably, the housing 22 is sufficiently rigid so that it does not collapse when grasped between the fingers of the user during ordinary use.

The housing 22 includes a side wall section 24 and an end wall section 26 that is integrally joined to the side wall section 24. In the embodiment illustrated in the drawings, the side wall section 24 includes a lower cylindrical segment 28 as well as an upper, funnel-shaped section 30. However, other configurations are also possible.

The side wall section 24 and the end wall section 26 present an internal wall surface 32 that defines a chamber 34. The chamber 34 has a central, longitudinal axis that is preferably parallel with a central, longitudinal axis of the housing 22. In areas adjacent the upper section 30, the cross-sectional configuration of the chamber 34 is funnel-shaped and decreases in area as the end wall section 26 is approached.

An outer end of the upper, funnel-shaped section 30 is connected to a flange 36. The flange 36 has an annular-shaped configuration in plan view, and extends in a reference plane that is perpendicular to the longitudinal axis of the chamber 34 and the housing 22. The flange 36, the upper segment 30 and the lower segment 28 are preferably integrally connected together and molded together as a unitary component.

The flange 36 surrounds an upper opening of the chamber 34 that is remote from the end wall section 26. A first sheet 38 of material is connected to the flange 36 and extends across the chamber 34 and the opening. In addition, a second sheet 40 of material extends across the chamber 34 and the opening and is connected to the housing 22 by an adhesive bond to the first sheet 38 in areas overlying the flange 36.

However, other constructions are also possible. For example, the second sheet 40 could be connected directly to the flange 36, and the first sheet 38 could be directly connected to the underside of the second sheet 40 in areas inwardly of the flange 36. As another option, the first sheet 38 could be connected to the flange 36 as shown, and the second sheet 40 connected to the first sheet 38 in areas inwardly of the flange 36. Moreover, the second sheet 40 could present an outwardly bulged configuration, and the first sheet 38 could present either an inwardly bulged configuration as shown or instead have a somewhat flat shape.

A first component 42 is received in the chamber 34 as illustrated in FIG. 2. In addition, a second component 44 is received in a compartment 46 that extends between the first sheet 38 and the second sheet 40. The compartment 46 is initially in non-communication with the chamber 34, so that the first component 42 does not inadvertently contact the second component 44.

Preferably, both of the sheets 38, 40 are made of a frangible material that can be ruptured when desired by a tool such as a hand-held applicator. An example of a suitable material for the sheets 38, 40 is a metallic foil such as aluminum foil having a thickness of 0.001 inch (0.025 mm).

The outer edges of the sheets 38, 40 are preferably fixed to each other by a heat seal adhesive bond. Additionally, the outer edge of the sheet 38 is fixed to the flange 36 by a heat seal adhesive bond. For example, one side of each sheet 38, 40 may be provided with a heat seal coating for connection to the underlying surface when heat is applied. Other options are also possible. For example, the sheet may be fixed to the flange 36 by an induction seal or by another type of adhesive, such as a pressure sensitive adhesive.

The housing 22 may be made of any suitable material that is compatible with the first component 42 and functions to retard degradation of the first component 42. If, for example, the first component 42 includes an acrylate, a suitable plastic for the housing 22 is polypropylene or polyethylene. Such plastics provide good oxygen permeability while also providing a barrier to the passage of volatile ingredients such as water or alcohol.

Preferably, at least part of the internal wall surface 32 has a plurality of protrusions to present a roughened texture. The protrusions facilitate mixing of the components 42, 44 once the sheets 38, 40 have been ruptured. The protrusions in certain circumstances may also function to disperse and retain the first component 42 over a relatively large surface area, so that contact and mixing with the second component 44 are facilitated once the sheets 38, 40 are ruptured.

Examples of suitable protruding structures include rods, cones, pyramids, truncated pyramids, ribs, bumps and fibers. The internal wall surface 32 may include a number of discreet recesses, grooves, cavities or pores that are spaced apart from each other or are interconnected with each other. Optionally, the internal end wall section 26 may also include protrusions if desired. Preferably, the protrusions extend inwardly generally toward a central longitudinal axis of the chamber 34.

Figure 3:
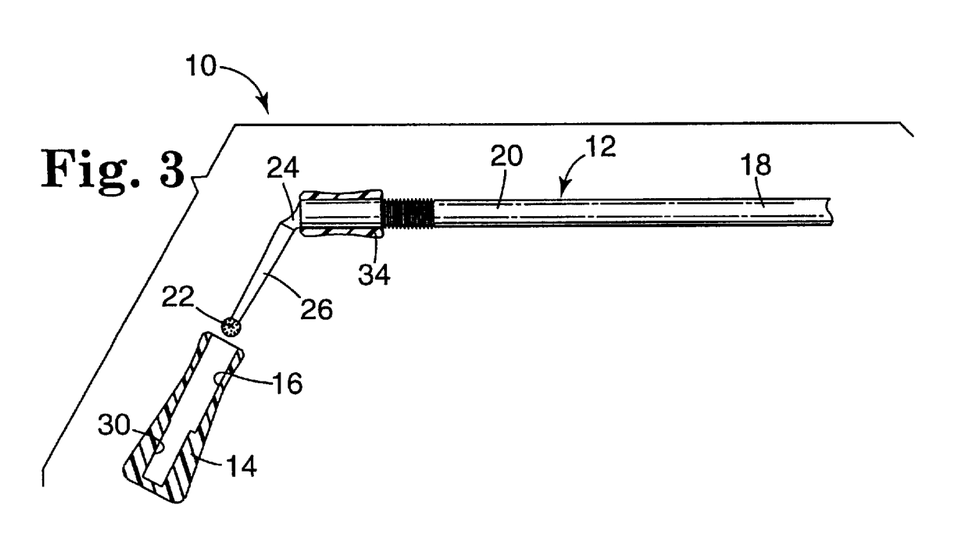
FIG. 3 is an enlarged cross-sectional view of the container shown in FIGS. 1–2, taken along lines 3—3 of FIG. 2.

In the illustrated embodiment, the protrusions are in the form of elongated ribs 48 that are shown in more detail in FIG. 3. The ribs 48 extend in a direction parallel to the longitudinal axis of the chamber 34 in the lower cylindrical segment 28. In FIG. 3, seven ribs 48 are spaced an equal distance apart from each other and extend inwardly toward the longitudinal axis of the chamber 34, although other arrangements are also possible. The ribs 48 are not shown in the remaining drawings for purposes of clarity. Optionally, the ribs 48 are made by a microstructure manufacturing technique, such as those described in applicant's U.S. Pat. No. 5,514,120 and PCT pending patent application WO 99/65704, both of which are expressly incorporated by reference herein.

Preferably, the container 20 has an outer configuration that is selected to orient the longitudinal axis of the chamber 34 in an upwardly inclined position as the opening is approached when the external wall surface of the container 20 is lying in a horizontal plane. In particular, the central axis of the cylindrical chamber segment 28 is inclined upwardly as the opening is approached whenever the container 22 is lying on a horizontal surface. As such any liquid material in the chamber 34 will tend to remain in the chamber 34 and not spill out from the container 20.

Figure 4:
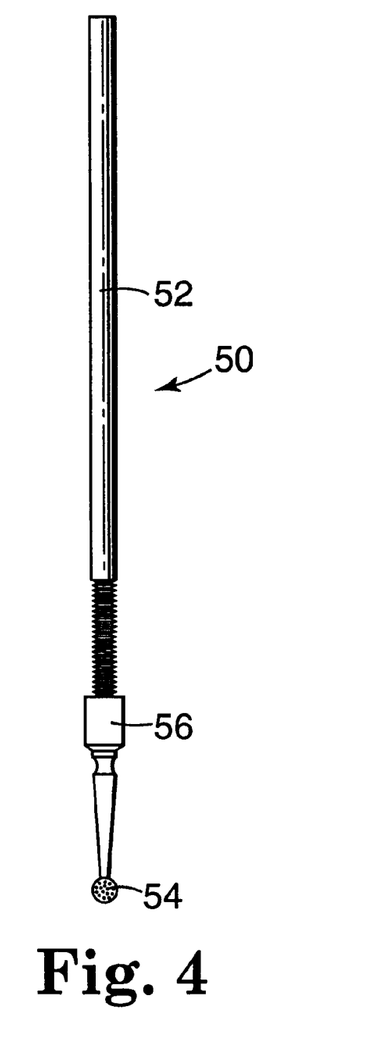
FIG. 4 is a reduced side elevational view of an applicator that is especially suitable for use with the container shown in FIGS. 1–3.

An applicator 50 that is particularly suitable for use with the container 20 is shown alone in FIG. 4. The applicator 50 includes an elongated, generally cylindrical shaft 52 having a tip 54 at one end. Preferably, the tip 54 includes a roughened surface to facilitate mixing of the components 42, 44. For example, the tip 54 could comprise a compressible, porous material such as a sponge, or comprise a plurality of fibers or other protrusions.

An example of a suitable applicator 50 is the "MICROBRUSH" brand applicator from Microbrush Corporation of Orlando, Fla. The "MICROBRUSH" brand applicator has a tip with a plurality of relatively short, flocked fibers. In addition to facilitating mixing of the components 42, 44 within the chamber 34, the flocked fibers also facilitate spreading of the resulting mixed composition across an application site, such as a prepared cavity surface of a tooth.

The applicator 50 also preferably includes structure for facilitating rupture of the sheets 38, 40. In the embodiment illustrated, the structure comprises a collar 56 that extends outwardly from the shaft 52 in directions perpendicular to the longitudinal axis of the shaft 52. The collar 56 preferably has a tapered front end that faces the tip 54, to facilitate tearing of the sheets 38, 40 when desired.

Alternatively, the protruding structure of the applicator 50 may have a shape other than the shape of the collar 56 shown in the drawings. For example, the protruding structure may incorporate a series of small pins, bars or pyramid-shaped bodies that are arranged in a circle about the periphery of the shaft 52. As another alternative, the protruding structure may be in the form of a cylindrical ring or sleeve. Preferably, the protruding structure extends outwardly from the shaft 52 a distance that is at least as great as the direction of extension of the tip 54 in reference planes perpendicular to the longitudinal axis of the shaft 52, in order to further reduce the likelihood that the tip 54 will contact the sheets 38, 40 as the tip 54 is moved past the sheets 38, 40 and out of the chamber 34.

Figure 5:
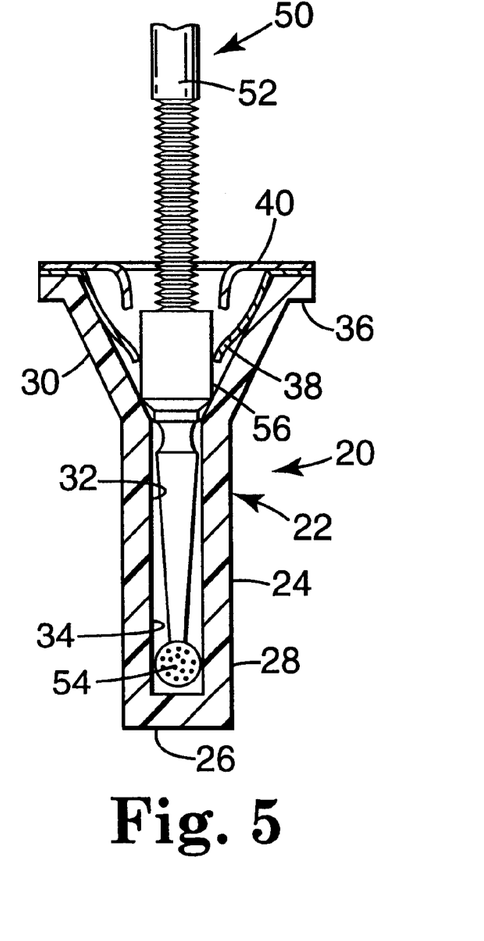
FIG. 5 is a fragmentary side cross-sectional view showing the applicator of FIG. 4 after it has been moved into the container of FIGS. 1–3.

FIG. 5 is an exemplary illustration of a possible use of the applicator 50 in combination with the container 20, except that the components 42, 44 are not shown in FIG. 5 for purposes of clarity. Initially, the applicator 50 is brought into a position over the container 20 such that the tip 54 contacts the second sheet 40. As the tip 54 is pressed against the second sheet 40, the second sheet 40 ruptures and presents an aperture. Continued movement of the applicator 50 in directions toward the chamber 34 causes the tip 54 to pass through the compartment 46 and contact the first sheet 38. The tip 54 is then pressed against the first sheet 38 until it also ruptures and presents an aperature.

As the first sheet 38 is ruptured, the second component 44 moves into the chamber 34, where it comes into contact with the first component 42. In addition, the applicator 50 is moved into the chamber 34 and toward the end wall section 26. Optionally, once the tip 54 is near the end wall section 26, the user can move the shaft 52 relative to the container 20 in a series of short, reciprocating back-and-forth motions so that thorough mixing of the components 42, 44 is assured. The back-and-forth motions of the tip 54 in the smaller section of the chamber 34 resembles a mixing action similar to the churning of butter.

The protrusions of the internal wall surface 32 function to facilitate mixing of the components 42, 44 as the tip 54 passes by the wall surface 32. In addition, the protruding structure of the tip 54 (such as the flocked fibers mentioned above) also facilitates thorough mixing of the components 42, 44. As the tip 54 passes across the wall surface 32, the components 42, 44 are directed through, in and across the protrusions which serve to enhance intermingling and thorough, uniform contact of the components 42, 44 with each other.

Preferably, the collar 56 is spaced from the outer end of the tip 54 a distance that is approximately equal or slightly less than the distance between the end wall section 26 and the junction between the lower segment 28 and the upper segment 30. Moreover, the collar 56 extends outwardly from the shaft 52 in directions generally perpendicular to the longitudinal axis of the applicator 50 a distance sufficient to prevent entry of the collar 56 into the lower cylindrical segment 28. As a result, the collar 56 serves as a stop to prevent contact of the tip 54 with the end wall section 26. By preventing contact of the tip 54 with the end wall section 26, the outer end of the tip 54 is not damaged. In addition, the mixed composition that is present on the tip 54 is not expressed away from the outer end of the tip 54 as might occur, for example, if the outer end of the outer end of the tip 54 was pressed against the end wall section 26.

Once the user is satisfied that the components 42, 44 are thoroughly mixed, the applicator 50 is withdrawn from the chamber 34. Advantageously, the additional tearing of the sheets 38, 40 provided by passage of the collar 56 reduces the likelihood that the sides of the tip 54 will contact the sheets 38, 40 as the tip 54 is subsequently withdrawn from the container 20. In this manner, the composition is not wiped away from the surface of the tip 54 by the sheets 38, 40, with the result that a greater quantity of the composition is available for transfer to the application site.

Figure 6:
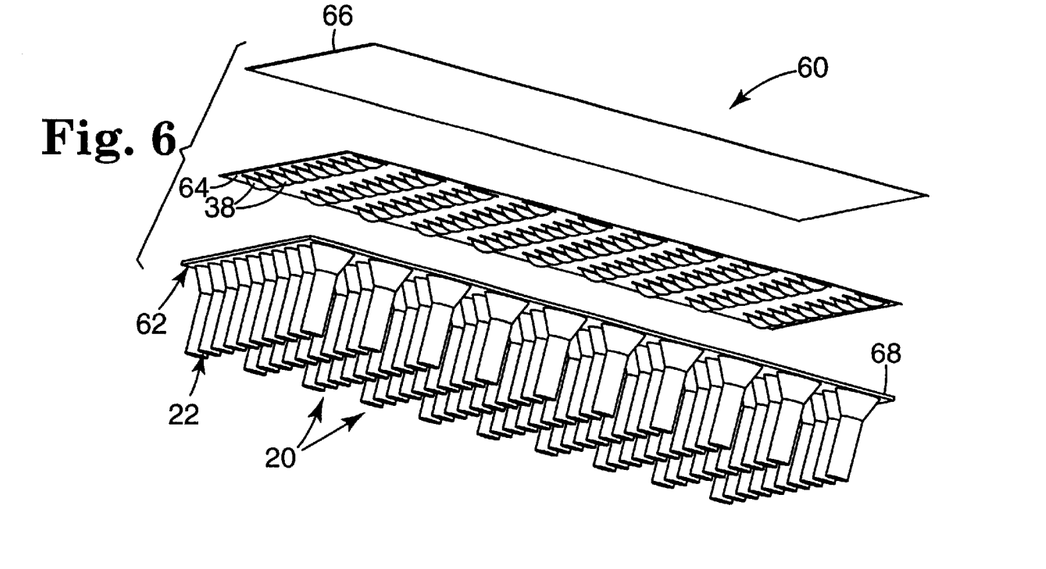
FIG. 6 is an exploded view of an array of storage and dispensing containers such as the container shown in FIGS. 1–3.
Figure 7:
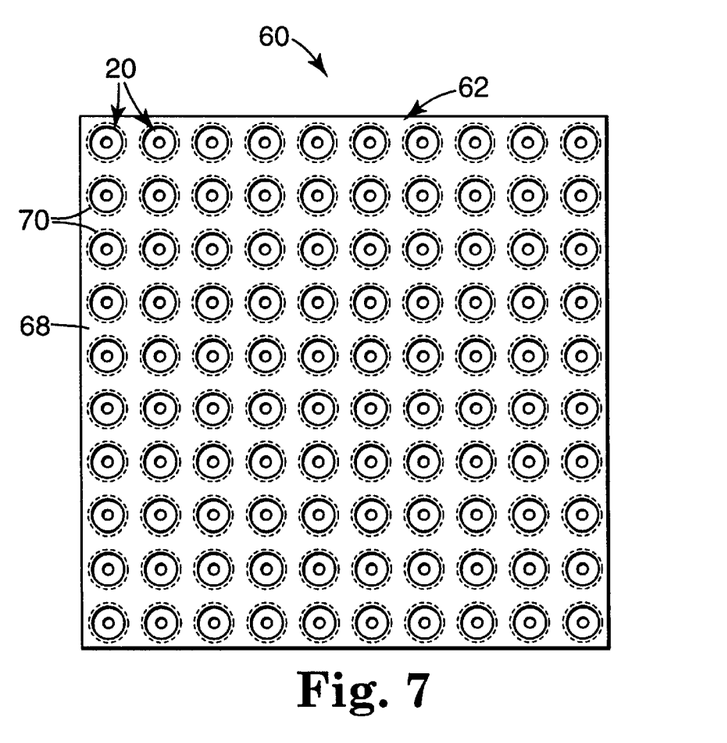
FIG. 7 is a top view a lower unit of the container array depicted in FIG. 6.

FIGS. 6 and 7 are illustrations of an exemplary set of containers 20 arranged in an array 60. FIG. 6 illustrates the array 60 in exploded format and as it might appear during manufacture before assembly. The number of containers 20 in the array 60 may vary from that shown in the drawings, and the array 60 may alternatively have containers 20 positioned in other arrangements as desired.

The array 60 includes a unit 62, a first film 64 and a second film 66. The unit 62 includes a number of housings 22 that are connected together by a flat substrate 68. Preferably, the substrate 68 and all of the housings 22 are integrally molded together as a single, unitary body.

A top view of the unit 62 alone is shown in FIG. 7. The substrate 68 includes lines of weakness 70 that, in this embodiment, extend in circles overlying the outer edge of each flange 36 (FIGS. 2 and 5). The lines of weakness 70 may be provided by forming a groove or a series of grooves or perforations in the substrate 68, or by any other suitable means.

The first film 64 and the second film 66 are co-terminus with the periphery of the substrate 68 in the illustrated embodiment. The first film 64 includes a number of formed bulged-shaped portions that provide the first sheet 38 described above and shown in FIG. 2. The second film 66 is planar and provides the second sheets 40 as mentioned above for each of the housings 22.

Preferably, the films 64, 66 are both cut in a circular pattern directly overlying each circular line of weakness 70. As such, the individual containers 20 may be detached from the array 60 as needed by grasping a housing 22 and bending the housing 22 relative to remaining housings 22 in the array 60. As the selected housing 22 is bent, the line of weakness 70 corresponding to that housing 22 fractures. In addition, the corresponding lines of weakness in the films 64, 66 overlying the selected housing 22 also rupture. The selected container 20 may then be detached from remaining containers 20 in the array 60.

The lines of weakness (such as the lines of weakness 70) of the array 60 described above are preferably circular in shape in order to avoid sharp edges in the vicinity of the flange 36. However, the lines of weakness may have other shapes as well. An example of an alternative pattern of lines of weakness is a rectangular grid having lines of weakness that extend between each adjacent pair of containers 20.

The array 60 is an advantage for the user, in that the containers 20 are kept in orderly fashion until detached by the user from remaining containers 20. Moreover, the array 60 is an advantage during manufacture, because automated dispensing apparatus having a similar, matching array of dispensing needles can be utilized to direct the components into all of the containers 20 (or at least a group of such containers 20) in simultaneous fashion. The array 60 also simplifies handling of multiple numbers of the containers 20 during manufacture, shipping and storage.

Figure 8:
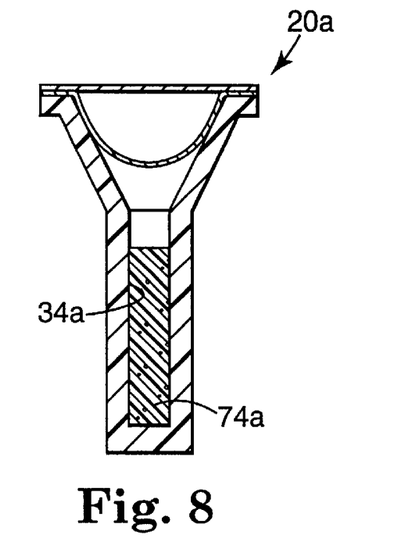
FIG. 8 is a view somewhat similar to FIG. 2, except that FIG. 8 illustrates a container according to another embodiment of the invention.

A storage and dispensing container 20a according to another embodiment of the invention is shown in FIG. 8. The container 20a is essentially the same as the container 20 described above, except that the container 20a includes a section of porous material 74a that is received in a chamber 34a of the container 20a. Other aspects of the container 20a are the same as the aspects of the container 20 described above, and as such a detailed description of those aspects need not be repeated.

Preferably, the porous material 74a is compressible. A suitable porous material 74a is a sponge such as a synthetic sponge made of polyurethane. The porous material 74a serves to hinder unintentional leakage or drippage of liquid components from the chamber 34a in instances where the container 20a is inverted. Moreover, the porous material 74a promotes mixing of components, especially in instances when the tip of the applicator compresses the porous material during the reciprocating mixing motion.

Figure 9:
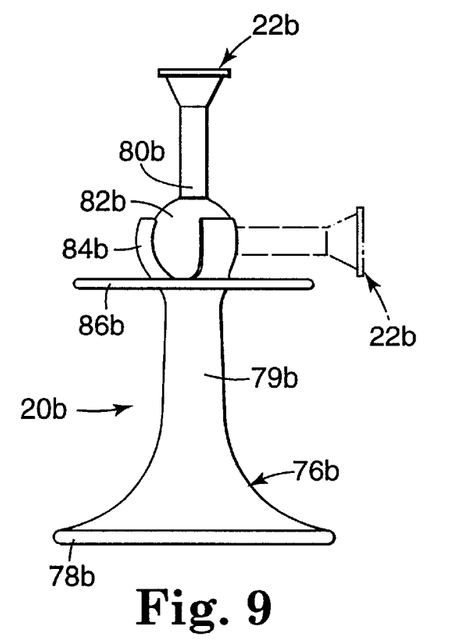
FIG. 9 is a side elevational view of a container that is constructed in accordance with a further embodiment of the invention.

A mixing and dispensing container 20b according to another embodiment of the invention is illustrated in FIG. 9. The container 20b includes a housing 22b having a somewhat funnel-shaped overall configuration with an inner chamber. Preferably, the container 20b includes two sheets (not shown) similar to the sheets 38, 40 that together define a compartment similar to the compartment 46. Preferably, a component is received in the compartment as well as in the chamber, in a manner similar to reception of the components 42, 44 in the compartment 46 and the chamber 34.

The container 20b includes an articulated holder 76b. The holder 76b includes an outer funnel-shaped end 78b that is connected by a stem 79b to a socket 84b. The socket 84b receives a ball-shaped segment 82b and includes a plurality of fingers that extend part of the way across the surface of the ball-shaped segment 82b. The segment 82b and the socket 84b together comprise a ball-and-socket joint which provides articulated movement between the holder 76b and the housing 22b.

The ball-shaped segment 82b is connected by a stem 80b to the housing 22b. Preferably, the fingers of the socket 84b are spaced sufficiently far apart from each other so that the stem 80b can be received between an adjacent pair of the fingers of the socket 84b when the holder 76b is oriented 90 degrees relative to the longitudinal axis of the stem 80b. In FIG. 9, an example of such a 90 degree orientation is shown by the dashed lines of the housing 22b.

Preferably, the container 20b also includes a disk-shaped support 86b that is adjacent the holder 76b. The support 86b is spaced from the end 78b a distance sufficient to receive the users fingers in the space between the support 86b and the end 78b. The support 86b enhances the user's grip on the container 20b, and as a result less effort is required to keep the container 20b in place between the user's fingers when desired.

Preferably, the holder 76b and the socket 84b are made of a plastic material than can withstand autoclaving, such as polyetheretherketone ("PEEK") or polysulfone ("PSU"). Preferably, the fingers of the socket 84b are sufficiently resilient so that the ball-shaped segment 82b is received in the socket 84b in snap-fit relation, using just enough pressure to deflect the fingers outwardly in order to receive the segment 82b. However, once the segment 82b is in place in the socket 84b, the fingers provide sufficient frictional resistance so that the orientation of the holder 76b relative to the housing 22b remains fixed during ordinary use once adjustment has been made, if necessary, to move the housing 22b to a desired position. The housing 22b may be made of polypropylene.

Figure 10:
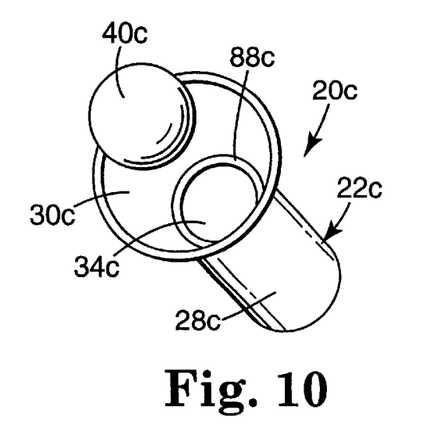
FIG. 10 is an exploded perspective view of a storage and dispensing container according to an additional embodiment of the invention.

Another embodiment of the invention is illustrated in FIG. 10. In FIG. 10, a container 20c includes a housing 22c with a lower, cylindrical segment 28c and an upper, funnel shaped segment 30c. However, in the container 20c, the housing 22c includes an annular shoulder 88c that is located between the lower segment 28c and the upper segment 30c.

A first sheet (not shown) is affixed to the shoulder 88c, and a second sheet 40c extends over the first sheet. A compartment, similar to the compartment 46 described above, is located between the first sheet and the second sheet 40c and receives a quantity of a second component. A quantity of a first component is received in a lower, cylindrical section of the chamber 34c that extends in the lower segment 28c.

Other aspects of the container 20c are similar to the container 20 described above. The container 20c may provide an advantage in certain instances in order to help avoid any spilling or splashing of the second component when the first and second sheets are ruptured. Additionally, the upper, funnel-shaped segment 30c helps to guide the applicator into a proper position for puncturing the sheets.

Figure 11:
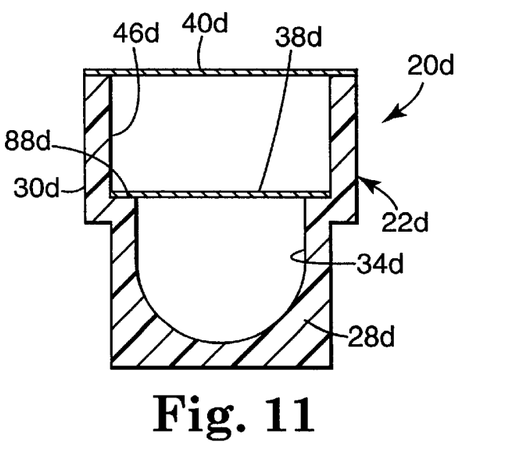
FIG. 11 is a side-cross sectional view of a storage and dispensing container according to still another embodiment of the invention.

A container 20d according to another embodiment of the invention is illustrated in FIG. 11. The container 20d includes a housing 22d having a lower segment 28d and an upper segment 30d. The lower segment 28d surrounds an internal chamber 34d having a semi-spherical bottom wall. An annular shoulder 88d extends in a plane that is perpendicular to a central axis of the container 20d.

A first sheet 38d is affixed to the shoulder 88d. In addition, a second sheet 40d is affixed to an outer end of the housing 22d. Optionally, both of the sheets 38d, 40d are affixed to the housing by an adhesive (such as a heat-seal coating), by ultrasonic bonding, by a pressure-sensitive adhesive or by any other suitable means.

The first sheet 38d is spaced from the second sheet 40d to present a compartment 46d. The compartment 46d receives a quantity of a second component (not shown). A first component is received in the chamber 34d below the first sheet 38d. Other aspects of the container 20d are similar to the container 20 described above.

The container 20d may also be modified to present additional compartments if desired. For example, the container 20d may include an additional internal shoulder and an additional film, so that three components may be held in isolation from each other until the films are ruptured to mix the components together. Optionally, the lower end wall may be replaced by a film in order to facilitate manufacturing.

Those skilled in the art will recognize that a variety of modifications and additions may be made to the embodiments that are shown in the drawings and described in detail above. For example, it is possible to combine aspects of several of the containers 20–20d if desired to provide a container that is not explicitly shown in the drawings. Moreover, some of the containers (such as containers 20, 20a, 20c and 20d) may be joined at their end walls (such as end wall 26) to present dual, oppositely oriented containers. Accordingly, the invention should not be limited to the exemplary containers described above, but instead only by a fair scope of the claims that follow along with their equivalents.

What is claimed is:

1. A storage and dispensing assembly comprising:
   a container including:
      a housing having wall sections defining a chamber with an opening;
      a first sheet extending across the chamber and connected to the housing;
      a second sheet extending across at least a portion of the first sheet and connected to the housing;
      a compartment located between the first sheet and the second sheet;
      a first component received in the chamber; and
      a second component received in the compartment, wherein the first sheet and the second sheet are rupturable in order to enable the fist component and the second component to mix together, and wherein at least a portion of the wall sections include a plurality of protrusions for facilitating mixing of the components; and
   an applicator having a tip and means on the tip for facilitating mixing of the first and second components after the first and second sheets are ruptured by the tip.

2. The storage and dispensing assembly according to claim 1 wherein the protrusions are part of a microstructured surface.

3. The storage and dispensing assembly according to claim 1 wherein the protrusions comprise a series of elongated ribs.

4. The storage and dispensing assembly according to claim 3 wherein the chamber has a longitudinal axis, and wherein the longitudinal axes of the ribs is generally parallel to the longitudinal axis of the chamber.

5. The storage and dispensing assembly according to claim 1 wherein the chamber has a generally constant transverse cross-sectional area in areas adjacent the plurality of protrusions as the opening is approached.

6. The storage and dispensing assembly according to claim 1 wherein the means for mixing comprises a roughened surface.

7. The storage and dispensing assembly according to claim 1 wherein the applicator further has a shaft and a tapered portion that decreases in cross-sectional area as the tip is approached.

8. The storage and dispensing assembly according to claim 7 wherein the chamber includes a shoulder and a bottom surface spaced from the shoulder, wherein the tip has an outer end, and wherein the tapered portion of the applicator is located at a distance from the outer end that is no greater than approximately the distance between the shoulder and the bottom surface.

9. The storage and dispensing assembly according to claim 1 wherein the first component and the second component comprise components of a dental composition.

10. The storage and dispensing assembly according to claim 9 wherein the dental composition is a dental adhesive or dental cement.

11. The storage and dispensing assembly according to claim 1 and including a holder and a coupling interconnecting the holder and the housing, wherein the coupling enables the housing to be shifted to any one of a number of positions relative to the holder when desired.

12. The storage and dispensing assembly according to claim 11 wherein the coupling is a ball-and-socket coupling.

13. The storage and dispensing assembly according to claim 1 wherein the housing includes at least one shoulder extending in the chamber, and wherein the first sheet is connected to the shoulder.

14. The storage and dispensing assembly according to claim 13 wherein the housing has an outer open end, and wherein the shoulder is spaced from the open end.

15. A method of dispensing a composition made from two or more components comprising:
   providing a container having an elongated chamber with a first component and a compartment with a second component, wherein the first component and the second component are initially separated from each other;

fracturing a rupturable sheet located between the chamber and the compartment with a tip of an applicator in order to enable the first component and the second component to contact each other; and moving the tip of the applicator along the longitudinal axis of the chamber in order to mix the first component and the second component, wherein the tip includes means for facilitating mixing of the components after the sheet is ruptured, and wherein the step of moving the tip of the applicator along the longitudinal axis of the chamber includes moving the first component and the second component adjacent a plurality of protrusions on an interior surface of the container to further facilitate mixing of the components.

16. The method of dispensing a composition made from two or more components according to claim 15 wherein the means for mixing comprises a roughened surface.

17. The method of dispensing a composition Made from two or more components according to claim 16 wherein the roughened surface of tip comprises a plurality of fibers.

18. The method of dispensing a composition made from two or more components according to claim 15 wherein the chamber has internal wall surfaces, and wherein at least a portion of the wall surfaces includes a plurality of protrusions.

19. The method of dispensing a composition made from two or more components according to claim 18 wherein the protrusions include a series of ribs.

* * * * *

UNITED STATES PATENT AND TRADEMARK OFFICE
CERTIFICATE OF CORRECTION

PATENT NO. : 6,419,414 B1  
DATED : July 16, 2002  
INVENTOR(S) : Bruce R. Broyles et al.

It is certified that error appears in the above-identified patent and that said Letters Patent is hereby corrected as shown below:

Title page should be deleted and substitute therefore the attached title page as shown on the attached page.

Signed and Sealed this

Seventh Day of September, 2004

JON W. DUDAS  
*Director of the United States Patent and Trademark Office*

(12) United States Patent
Broyles et al.

(10) Patent No.: US 6,419,414 B1
(45) Date of Patent: Jul. 16, 2002

(54) CONTAINER FOR MULTIPLE-COMPONENT COMPOSITIONS (75) Inventors: Bruce R. Broyles, Oakdale; Robert W. Petrich, Woodbury; Robert Lee, Lake Elmo; Darin J. Meyertholen, Woodbury, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/838,875

(22) Filed: Apr. 20, 2001

(51) Int. Cl.$^7$ .................................................. B43K 5/14
(52) U.S. Cl. ......................... 401/132; 401/134; 206/219
(58) Field of Search ........................... 401/132–135, 401/123, 127–130; 206/219, 222

(56) References Cited

U.S. PATENT DOCUMENTS

| | | |
|---|---|---|
| 2,612,163 A | 9/1952 | Norman |
| 2,624,011 A | 12/1952 | Stern |
| 2,862,616 A | 12/1958 | Capozzi et al. |
| 3,340,873 A | 9/1967 | Solowey |
| 3,359,361 A | 12/1967 | Oakman |
| 3,554,705 A | 1/1971 | Johnston et al. |
| 3,613,697 A | 10/1971 | Andrews |
| 4,152,269 A | 5/1979 | Babson |
| 4,537,303 A | 8/1985 | Muhlbauer |
| 4,828,419 A | 5/1989 | Porter et al. |
| 4,845,923 A | * 7/1989 | Donovan ..................... 206/365 |
| 4,912,048 A | * 3/1990 | Smith et al. ................. 206/219 |
| 4,952,204 A | 8/1990 | Korteweg |
| 5,322,165 A | * 6/1994 | Melker et al. ............... 206/365 |
| 5,514,120 A | 5/1996 | Johnston et al. |
| 5,660,273 A | 8/1997 | Discko, Jr. |
| 5,735,437 A | 4/1998 | Broyles et al. |
| 5,743,736 A | 4/1998 | Folko et al. |
| 5,860,806 A | 1/1999 | Pranitis, Jr. et al. |
| 5,874,045 A | 2/1999 | Chisum |
| 5,989,229 A | 11/1999 | Chiappetta |
| 6,095,813 A | 8/2000 | Broyles |
| 6,105,761 A | 8/2000 | Peuker et al. |

FOREIGN PATENT DOCUMENTS

WO    WO 99/65704    12/1999

OTHER PUBLICATIONS

Microbrush, "Dispenser Series Disposable Applicator", 1 page.
Microbrush & Ultrabrush, "Dispenser Series Instructions for Assembly", 1 page.
Microbrush, ProTouch, Disposable Touch–Up Microbrush.
Pending U.S. Ser. No. 09/838,883, filed Apr. 20, 2001.

* cited by examiner

Primary Examiner—Gregory L. Huson
Assistant Examiner—Tuan Nguyen
(74) Attorney, Agent, or Firm—James D. Christoff (57) ABSTRACT

A container includes an inner chamber and one or more compartments that hold components of a composition apart from each other until needed for use. The container includes two or more sheets that are ruptured for mixing the components together when desired. In certain embodiments, the container includes an inner surface with a plurality of protrusions to facilitate mixing and dispensing of the mixed composition. In other embodiments, the container includes an articulated holder that enables the user to adjust the configuration of the container to any one of a number of orientations.

19 Claims, 4 Drawing Sheets